United States Patent
Shechterman (10) Patent No.: US 9,798,131 B2
(45) Date of Patent: Oct. 24, 2017

(54) ROTATABLE OBLIQUE-VIEWING STEREOENDOSCOPE

(71) Applicant: Visionsense Ltd., Petah Tikva (IL)

(72) Inventor: Mark Shechterman, Nes-Ziona (IL)

(73) Assignee: Visionsense Ltd., Petah Tikva (IL)

( * ) Notice: Subject to any disclaimer, the term of this patent is extended or adjusted under 35 U.S.C. 154(b) by 134 days.

(21) Appl. No.: 14/962,688

(22) Filed: Dec. 8, 2015

(65) Prior Publication Data
US 2016/0178886 A1  Jun. 23, 2016

(30) Foreign Application Priority Data
Dec. 23, 2014  (IL) ......................................... 236418

(51) Int. Cl.
| | | |
|---|---|---|
| H04N 7/12 | (2006.01) | |
| H04N 11/02 | (2006.01) | |
| H04N 11/04 | (2006.01) | |
| G02B 23/24 | (2006.01) | |
| A61B 1/00 | (2006.01) | |
| G02B 23/08 | (2006.01) | |
| H04N 13/02 | (2006.01) | |

(52) U.S. Cl.
CPC ...... *G02B 23/2415* (2013.01); *A61B 1/00096* (2013.01); *A61B 1/00183* (2013.01); *A61B 1/00193* (2013.01); *G02B 23/08* (2013.01); *G02B 23/243* (2013.01); *G02B 23/2453* (2013.01); *H04N 13/0203* (2013.01)

(58) Field of Classification Search
None
See application file for complete search history.

(56) References Cited

U.S. PATENT DOCUMENTS

| | | |
|---|---|---|
| 4,061,135 A | 12/1977 | Widran et al. |
| 4,924,853 A | 5/1990 | Jones, Jr. et al. |
| 5,527,263 A | 6/1996 | Zobel et al. |
| (Continued) | | |

FOREIGN PATENT DOCUMENTS

| | | |
|---|---|---|
| WO | WO 2010/014421 | 2/2010 |
| WO | 2013/038403 A2 | 3/2013 |
| WO | WO 2013/155192 | 10/2013 |

OTHER PUBLICATIONS

Extended European Search Report for European Patent Application No. 15003506.1, mailed Sep. 1, 2016.

*Primary Examiner* — Talha M Nawaz
(74) *Attorney, Agent, or Firm* — Merchant & Gould P.C.

(57) ABSTRACT

Rotatable, oblique-viewing stereoendoscope including a dual-pupil aperture divided to a first pupil and a second pupil, a proximal objective assembly positioned proximally to the dual-pupil aperture, a first image sensor configured to detect a first image focused by the proximal objective assembly and a second image sensor configured to detect a second image focused by the proximal objective assembly, a relay system positioned distally to the dual-pupil aperture and a front optical system positioned distally to the relay system, the front optical system including a folding prism, wherein the front optical system is configured to reimage the dual-pupil aperture at a distal end thereof, thereby producing an image of the first pupil and an image of the second pupil at a distal pupil plane and wherein the stereoendoscope does not include a negative power lens positioned distally to the folding prism.

8 Claims, 5 Drawing Sheets

(56) References Cited

U.S. PATENT DOCUMENTS

| | | | |
|---|---|---|---|
| 5,538,497 A | 7/1996 | Hori | |
| 5,588,948 A | 12/1996 | Takahashi et al. | |
| 5,689,365 A | 11/1997 | Takahashi | |
| 5,720,706 A | 2/1998 | Takahashi et al. | |
| 5,743,847 A | 4/1998 | Nakamura et al. | |
| 5,751,341 A | 5/1998 | Chaleki et al. | |
| 5,825,534 A | 10/1998 | Strähle | |
| 5,895,350 A | 4/1999 | Hori | |
| 5,964,696 A * | 10/1999 | Mihalca | A61B 1/00193 348/45 |
| 6,139,490 A | 10/2000 | Breidenthal et al. | |
| 6,817,975 B1 | 11/2004 | Farr et al. | |
| 7,101,334 B2 | 9/2006 | Takahashi | |
| 7,559,891 B2 | 7/2009 | Farr et al. | |
| 8,081,380 B2 | 12/2011 | McKinley | |
| 8,118,730 B2 | 2/2012 | Farr et al. | |
| 8,149,270 B1 | 4/2012 | Yaron et al. | |
| 2005/0159641 A1 | 7/2005 | Kanai | |
| 2009/0076329 A1* | 3/2009 | Su | A61B 1/0008 600/134 |
| 2012/0184819 A1 | 7/2012 | Farr et al. | |
| 2013/0176395 A1* | 7/2013 | Kazakevich | A61B 1/00193 348/45 |
| 2014/0364693 A1* | 12/2014 | Shechterman | A61B 1/00193 600/111 |
| 2015/0257629 A1* | 9/2015 | Shahinian | A61B 1/00087 600/106 |

* cited by examiner

ROTATABLE OBLIQUE-VIEWING STEREOENDOSCOPE

FIELD OF THE DISCLOSED TECHNIQUE

The disclosed technique relates to oblique-viewing stereoendoscopes, in general, and to oblique-viewing stereoendoscopes that can be rotated to change the field of view, in particular.

BACKGROUND OF THE DISCLOSED TECHNIQUE

Rotatable, oblique-viewing stereoendoscopes are known in the art. A stereoendoscope acquires stereoscopic images. An oblique-viewing stereoendoscope includes a prism for folding the Field of View (FOV) of the endoscope. That is, the prism changes the Direction of View (DOV) of the endoscope from a zero angle DOV to an oblique angle DOV. A rotatable oblique-viewing stereoendoscope can be rotated about the longitudinal axis thereof for changing the FOV of the endoscope. It is noted that the parallax between the images acquired by the stereoendoscope should be maintained horizontally leveled for allowing stereopsis.

Reference is now made to U.S. Pat. No. 5,689,365, issued to Takahashi, and entitled "Stereoscopic-Vision Endoscope". This publication relates to a stereoscopic-vision endoscope having an objective optical system and a rear optical system. The objective optical system is positioned infront of the rear optical system. The objective optical system has a single optical axis and includes an oblique-vision observation optical system (e.g., a prism folding the Field of View—FOV—of the endoscope relative to the tube axis). The rear optical system has a plurality of optical axes. The front and rear optical systems can be turned relative to each other, thereby changing the tilted Direction of View (DOV) of the endoscope.

It is noted that the objective optical system includes a negative power, diverging, lens (e.g., lens 14b of FIG. 7) located in front of the folding FOV prism (e.g., prism 14c of FIG. 7). The front negative lens does not perform reimaging the pupils distally to the prism. The front diverging lens is directed at decreasing beam wandering inside this folding prism. That is, light beams arriving at the diverging lens from wide angles are diverged such that they are reflected from the folding prism, and do not enter the endoscope to smaller angles such that they are reflected twice, without vignetting, inside FOV folding prism. Thereby, the negative lens limits the FOV of the endoscope.

Reference is now made to U.S. Pat. No. 5,743,847, issued to Nakamura et al., and entitled "Stereoscopic Endoscope Having Image Transmitting Optical-System and Pupil Dividing Unit That Are Axially Movable with Respect to Each Other". This publication relates to a rigid stereoscopic endoscope including an inserting portion, an operational holding portion and a pupil dividing means. The inserting portion is coupled with the operational holding portion. The operational holding portion and the pupil dividing means are rotatable relative to each other. The inserting portion incorporates an objective lens consisting of a plurality of lenses including a prism for oblique-vision observation, and a relay lens portion consisting of a plurality of lens groups from its distal end side. It is noted that the rigid stereoscopic endoscope includes a negative power lens positioned in front of (i.e., distally to) the oblique-vision prism (as can be seen in FIG. 2). As mentioned above, the front negative lens does not perform reimaging the pupils distally to the prism and limits the FOV of the endoscope.

Reference is now made to U.S. Pat. No. 5,825,534, issued to Strahle, and entitled "Stereoendoscope Having a Folded Sight Line". This publication relates to a stereoendoscope having a sight line folded relative to the tube axis. The endoscope includes an endoscope tube and a viewing component. The endoscope tube and the viewing component are rotatable with respect to each other so that the line of sight can be changed. The endoscope tube includes distal front optics, including a deflecting prism, a negative refractive power component and a proximal component having a positive refractive power. The deflecting prism is mounted between the negative refractive power component and the proximal positive refractive power component. As mentioned above, a front negative refractive power component does not perform reimaging the pupils distally to the prism and limits the FOV of the endoscope.

Reference is now made to U.S. Pat. No. 5,588,948, issued to Takahashi et al., and entitled "Stereoscopic Endoscope". This publication relates to a stereoscopic endoscope including an inserting section, and a pupil dividing device, rotatable with respect to each other. The inserting section includes an objective lens system and an image transmission device coaxially arranged with the objective lens system. The objective lens system includes folding prism and a negative lens positioned in front of the prism (as can be seen, for example, in FIGS. 7, 13a and 15). As mentioned above, a front negative refractive power component does not perform reimaging the pupils distally to the prism and limits the FOV of the endoscope.

SUMMARY OF THE PRESENT DISCLOSED TECHNIQUE

It is an object of the disclosed technique to provide methods and systems for oblique-view stereoendoscopy. In accordance with an embodiment the disclosed technique, there is thus provided a rotatable, oblique viewing stereoendoscope. The stereoendoscope includes a dual pupil aperture, a proximal objective assembly, a first and a second image sensors, a relay system, a front optical system, and a folding prism. The dual pupil aperture is divided to a first pupil and a second pupil, each receiving a respective image of an object. The proximal objective assembly is positioned proximally to the dual pupil aperture and focuses the images. The image sensors detect the images focused by the proximal objective assembly. The relay system is positioned distally to the dual pupil aperture and transmits the images toward the dual pupil aperture. The front optical system is positioned distally to the relay system. The front optical system reimages the dual pupil aperture at a distal end thereof. The front optical system produces the images from the reflected light received through the pupils. The folding prism receives light reflected from the object and directs the reflected light at an oblique angle toward the relay system. The folding prism is rotatable such that a direction of view of the stereoendoscope can be rotated about a longitudinal axis of the relay system.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a rotatable, oblique-viewing stereoendoscope including a rotatable folding prism, a front optical system, a relay system, a dual-pupil aperture, a proximal objective assembly, and a pair of image sensors. The image sensors detect stereoscopic images of an object. The proximal objective assembly focuses the stereoscopic images on the images sensors. The dual-pupil aperture is positioned distally to the proximal objective assembly. The dual-pupil aperture is divided into two adjacent pupils. Specifically, a first pupil receives a first image of the object and a second pupil receives a second image of the object.

The relay system is positioned distally to the dual-pupil aperture and transmits the images toward the dual-pupil aperture. It is noted that the relay system alternately reimages the dual-pupil aperture and the object plane therewithin. That is, the relay system produces an intermediate image of the dual-pupil aperture at a first location, followed by an intermediate image of the object plane at a subsequent location, and so on.

The front optical system is positioned distally to the relay system. The front optical system reimages the dual-pupil aperture at a distal end thereof. Put another way, the front optical system produces an image of the first pupil and an image of the second pupil at a distal pupil plane. It is noted that at the distal pupil plane, the image of the first pupil is spatially separated from the image of the second pupil thereby defining the Inter Pupillary Distance (IPD) of the endoscope. The front optical system produces the first image from the light reflected from the object and received through the image of the first pupil, and produces the second image from the light reflected from the object and received through the image of the second pupil.

The rotatable folding prism redirects light reflected from an object toward the front optical system. That is, the folding prism makes the endoscope an oblique-viewing endoscope. Additionally, the rotatable folding prism is rotatable with respect to the front optical system. In this manner, a Direction of View (DOV) of the stereoendoscope can be rotated about a longitudinal axis of the front and relay optical system. In accordance with another embodiment of the disclosed technique, the front optical system is rotated along with the folding prism with respect to the relay system and the dual-pupil aperture, and in accordance with yet another embodiment of the disclosed technique, the front optical system and the relay system rotate together with the folding prism with respect to the dual-pupil aperture.

The optical system (i.e., the relay system and the front optical system) reimages the dual-pupil aperture, thereby producing dual-pupil image planes. The stereoendoscope of the disclosed technique does not include a negative lens (or a negative lens assembly) distally to the most distal reimaged dual-pupil plane. Thereby, the Field of View (FOV) of the stereoendoscope of the disclosed technique is wide (e.g., FOV of 90 degrees). Put another way, the stereoendoscope of the disclosed technique, does not include a negative lens distally to folding prism.

Figure 01A:
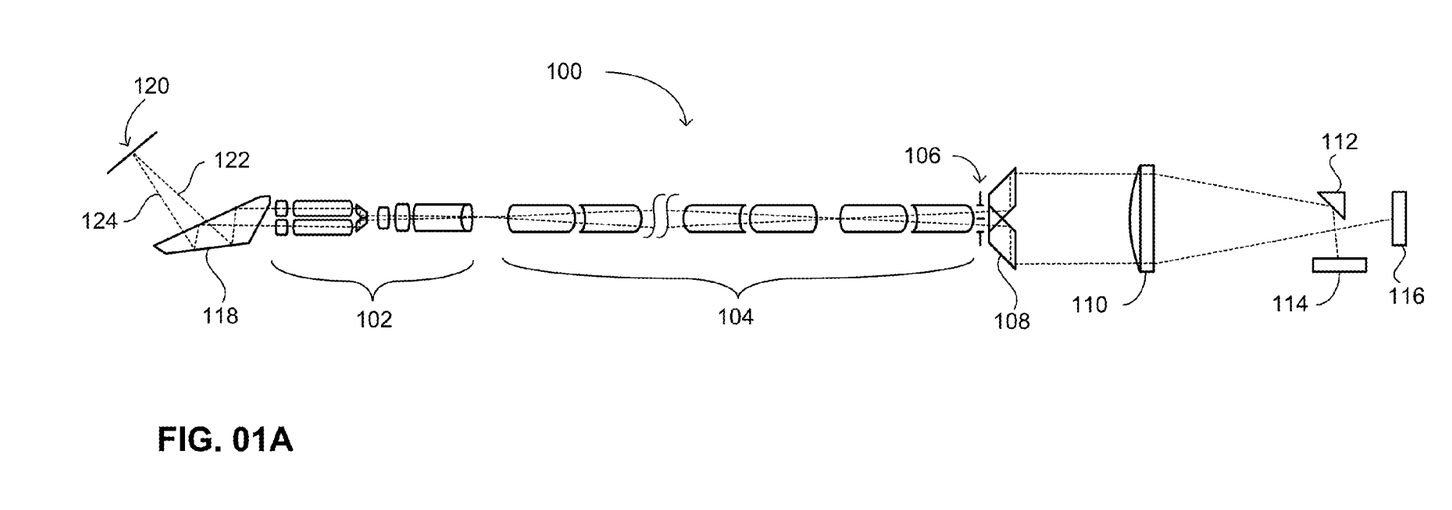
FIGS. 1A and 1B are schematic illustrations of a rotatable, oblique-viewing stereoendoscope, constructed and operative in accordance with an embodiment of the disclosed technique.
Figure 01B:
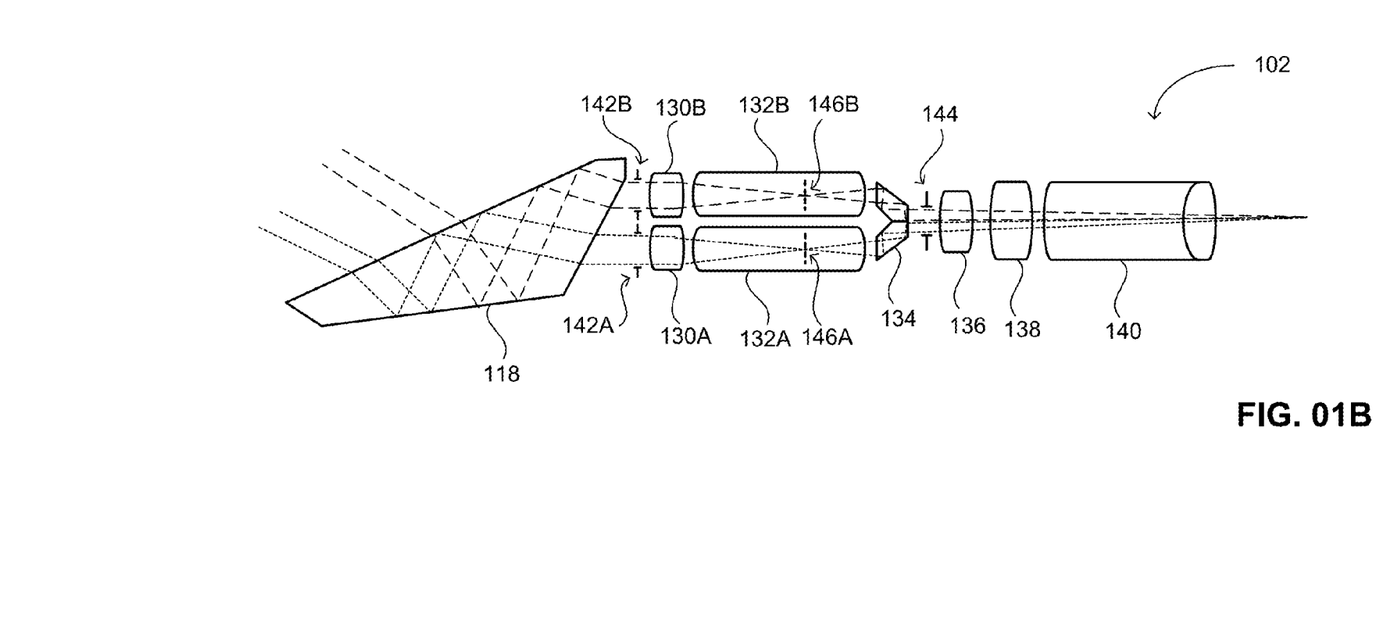

Reference is now made to FIGS. 1A and 1B, which are schematic illustrations of a rotatable, oblique-viewing stereoendoscope, generally referenced 100, constructed and operative in accordance with an embodiment of the disclosed technique. FIG. 1A depicts the optical components of the endoscope, and FIG. 1B depicts a front optical system and a folding prism of the endoscope in a magnified manner. Stereoscopic endoscope 100 includes a front optical system 102, a relay optical system 104, a dual-pupil aperture 106, a pair of proximal periscope prisms 108, a proximal objective lens assembly 110, a channel separator 112, two sensors 114 and 116, and a rotatable folding prism 118.

Front optical system 102 is optically coupled between rotatable folding prism 118 (positioned distally to front optical system 102) and relay optical system 104. Dual-pupil aperture 106 is optically coupled between relay optical system 104 and proximal periscope prisms 108. Proximal objective lens assembly 110 is optically coupled between proximal periscope prisms 108 and channel separator 112. Channel separator 112 is further optically coupled with at least one of sensors 116.

An object plane 120 is positioned distally to folding prism 118 and at an angle with respect to the optical axis of relay system 104. Object plane 120 represents the surface of an object (or a scene) to be imaged. Object plane 120 is illuminated by a light source (not shown) either directly or through means, such as a fibers bundle or a light-guide.

Rotatable folding prism 118 is configured to fold the optical axis of endoscope 100 such that its FOV would be inclined at an oblique angle with respect to the optical axis of relay system 104. In the example set forth in FIGS. 1A and 1B, the folding prism is a double folding prism reflecting the light twice, and the folding prism folds the FOV of endoscope 100 by an angle of 30°. Alternatively, the folding angle of the prism can be any angle ranging between 0-90 degrees.

Additionally folding prism 118 is rotatable and can rotate about the longitudinal axis (not shown) of relay system 104, thereby changing the DOV of endoscope 100. Rotatable folding prism 118 transmits light reflected from object plane 120 onto front optical system 102. It is noted that in every direction that folding prism 118 is directed to, folding prism 118 projects a plane toward front optical system 102 and the projected plane is stereoscopically imaged by endoscope 100. As folding prism 118 is the only component that rotates, the stereoscopic image is always aligned and no other image direction alignment is required. Specifically, the projected plane (e.g., object plane 120) is always imaged such that the parallax between two optical channels of the endoscope (i.e., forming the stereoscopic image) is horizontal. In other words, for each rotation direction of prism 118, the prism would project a plane (e.g., object plane 120) onto front optical system 102. This projected plane would always (i.e., for every rotation angle) be imaged with a horizontal parallax allowing for stereopsis.

Front optical system 102 reimages the pupils of endoscope 100 (i.e., dual-pupil aperture 106) at a point distal to front optical system 102. Specifically front optical system 102 reimage the pupils of endoscope 100 to a plane positioned between front optical system 102 and folding prism 118, as seen in FIG. 1B—reimaged pupils 142A and 142B.

Thereby, object plane 120 as projected by folding prism 118 is received by the reimaged pupils and therefrom enters endoscope 100 and is eventually stereoscopically imaged. In the opposite direction, front optical system 102 transmits light reflected from object plane 118 in two separate channels 122 and 124 toward relay system 104 (each running between the reimaged respective pupil distal to front lens system 102 to a respective one of sensors 114 and 116). The components and configuration of front lens assembly 102 is detailed further herein below with reference to FIG. 1B.

Relay system 104 is both object imaging and pupil imaging. In particular, relay system 104 is constructed of repeating sub-chains which produce a series of object images and additionally produce a series of pupil plane images. A reimaged object relates to a plane perpendicular to the optical axis (not shown) of the optical relay system, in which an image of the object is produced by the optical relay system. A reimaged pupil plane is a plane perpendicular to the optical axis of the optical relay system, in which the aperture stop is reimaged. At the reimaged pupil plane, the light beams from the object are fully separated according to the distal prism through which the light beams entered the relay system. That is, the stereoscopic image pair is fully separated at each of the pupil plane images.

Additionally, relay system 104 maintains the entering light beams therewithin by employing converging and diverging lenses in each of its sub-chains. Further additionally, relay system 104 relays the stereoscopic images of object plane 120 with reduced aberrations. The structure and operation of relay lens system is detailed further herein below with reference to FIG. 2.

Relay system 104 transmits the entering light beams through dual-pupil aperture 106 and onto proximal periscope prisms 108. Dual-pupil aperture 106 is constructed of an aperture stop and an opening (both not shown). The shape of dual-pupil aperture 106 (i.e., the shape of the opening of the aperture stop) corresponds to the cross section shape of the optical relay system. Dual-pupil aperture 106 is divided into two pupils defining the two channels of endoscope 100. The pupils of dual-pupil aperture 106 complement each other for substantially fully covering the opening of dual-pupil aperture 106. Thereby the pupils of dual-pupil aperture complement each other for substantially forming together the cross section shape of the optical relay system. Each pupil of dual-pupil aperture 106 receives light beams respective of a different perspective of object plane 120. In this manner, the single axis relay system 104 transmits two images, respective of two perspectives of object plane 120. The structure and operation of dual-pupil aperture 106 is detailed further herein below with reference to FIG. 3.

Proximal periscope prisms 108 receive the entering light beams from dual-pupil aperture 106. Proximal periscope prisms 108 transmit the entering light beams onto proximal object lens assembly 110 and channel separator 112. Proximal periscope prisms 108 enlarge the distance between beams from each of the pupils of dual-pupil aperture 106 for adjusting the angular and spatial separation between those light beams for purpose of proper beam separation, such that each image would be directed to the respective one of sensors 114 and 116. Proximal periscope prisms 108 are further detailed herein below with reference to FIGS. 4A, 4B and 4C.

Proximal objective lens assembly 110 includes at least one objective lens for focusing beams exiting proximal periscope prisms 112 onto sensors 114 and 116. Each of sensors 114 and 116 detects a respective image of object plane 120 received from a different perspective (due to the IPD between the reimaged pupils at the distal end of the front optical system). Thereby, stereoendoscope 100 acquires a stereoscopic image of object plane 120.

As can be seen in FIG. 1A, folding element 112 folds one the channels toward image sensor 114, while the other channel travels to sensor 116 (passing aside of folding element 112). In this manner, each channel (i.e., each image of the stereoscopic image pair) is detected by a different image sensor. Alternatively, other configurations for directing each of the light channels toward each of sensors 114 and 116 can be employed. For example a channel separator can be positioned on the path of both channels and direct the channels toward the sensors according to their approach angle to the separator. The channel separator can be, for instance, a total internal reflection channel separator. Further alternatively, each sensor can be positioned on the path of a respective one of the channels at the output of objective assembly 110.

Each of sensors 114 and 116 detects a respective one of the different perspectives images of object plane 120, and provides the data to a processor (not shown) for producing a stereoscopic image of object plane 120. Each of proximal periscope prisms 108, proximal objective lens assembly 110, folding element 112 and sensors 114 and 116 are positioned at the proximal end of endoscope 100 and outside of the body of a patient. Therefore those elements are not subject to the physical constraints of minimally invasive surgery and can be of any size. Thereby, the size and resolution of sensors 114 and 116 can be increased to increase the Nyquist frequency of endoscope 100, thereby avoiding aliasing of the stereoscopic images.

With reference to FIG. 1B, front optical system 102 includes a first channel lens assembly (not referenced—e.g., a left channel), a second channel lens assembly (not referenced—e.g., a right channel), proximal periscope prisms 118, and a common lens assembly (not referenced). Each of the first and the second lens assemblies direct light received from different perspectives of object plane 120 toward proximal periscope prisms 108. Proximal periscope prisms 108 direct the light into the common lens assembly and therethrough toward relay system 104.

The common lens assembly includes lenses 136 138 and 140. The common lens assembly reimages dual-pupil aperture 106 as reimaged dual-pupil aperture 144, which is positioned proximally to distal periscope prisms 134. Additionally, the common lens assembly reimages the images of object plane 120, formed by the first and the second (e.g., left and right) lens assemblies, and directs the images toward relay system 104.

The first lens assembly includes lenses 130A and 132A, and the second lens assembly includes lenses 130B and 132B. In the examples set forth in FIGS. 1A and 1B, the first lens assembly transmits an image of object plane 120 from a left perspective, and the second lens assembly transmits an image of object plane 120 from a right perspective, for forming together a stereoscopic image of object plane 120. The first and the second lens assemblies reimage the pupils of dual-pupil aperture 106 as reimaged pupils 142A and 142B. As can be seen in FIG. 1B, reimaged pupils 142A and 142B are positioned distally to the first and second lens assemblies. Thereby, light reflected from object plane 120 and directed by folding lens 118 is received by pupils 142A and 142B and enters endoscope 100. Reimaging the pupils of endoscope 100 (e.g., the pupils of dual-pupil aperture 106 that define the light channels of endoscope 100) to the distal end of the optical system enables endoscope 100 to have a wide FOV.

For enabling a wide FOV, endoscope 100 does not include a negative lens (or a negative lens assembly) at the distal end thereof. Such a negative lens would have diverged the entering light, thereby limiting the entrance angle of the endoscope. Put another way, lenses 130A and 132A and lenses 130B and 132B of the first and the second lens assemblies, respectively, are positive power lenses. Alternatively, one of lenses 130A and 132A is negative and the other one is a positive lens of higher optical power, such that the lens assembly is a positive power lens assembly. Thus, by omitting such distal negative lenses the FOV of endoscope 100 is increased.

Additionally, reimaged pupils 142A and 142B are spatially separated from each other, thereby defining the Inter Pupillary Distance (IPD) of endoscope 100. In this manner, endoscope 100 transmits two channels having an IPD defined by the distance between reimaged pupils 142A and 142B via a single axis relay system 104 to be detected by two sensors 114 and 116. Additionally, each of the first lens assembly and the second lens assembly reimages object plane 120 as reimaged object planes 146A and 146B, respectively. Specifically, reimaged object plane 146A is an image of object plane 120 as seen from a left perspective, and reimaged object plane 146B is an image of object plane 120 as seen from a right perspective. The first lens assembly and the second lens assembly transmit reimaged object planes 146A and 146B toward the prisms 134 and further toward the common lens assembly and relay system 104.

As mentioned above, stereoendoscope 100 has a wide FOV (e.g., due to the lack of negative lenses distally to the folding prism). Thereby, size of the folding prism can be reduced while maintaining a sufficient size of an imaged field. For example, the folding prism and all other components of stereoendoscope 100 are fitted within a 10 mm endoscope.

Figure 2:
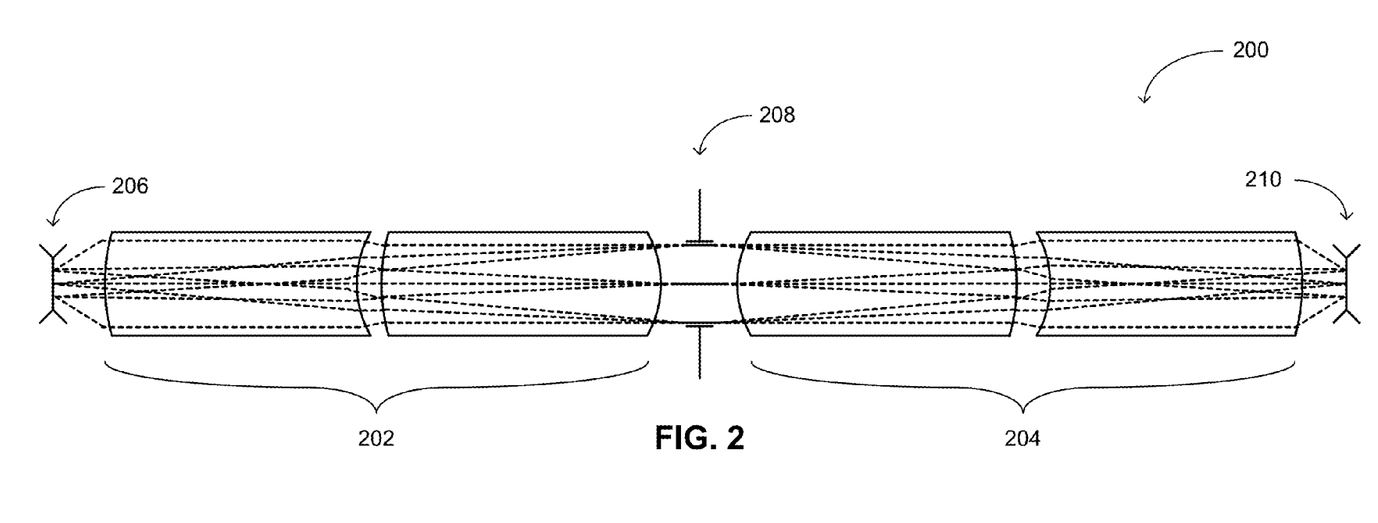
FIG. 2 is a schematic illustration of a pair of rod lenses sub-chains, forming together with other such rod lenses sub-chains a relay system, constructed and operative in accordance with another embodiment of the disclosed technique.

Reference is now made to FIG. 2, which is a schematic illustration of a pair of rod lenses sub-chains, generally referenced 200, forming together with other such rod lenses sub-chains a relay system, constructed and operative in accordance with another embodiment of the disclosed technique. Rod lenses sub-chains pair 200 includes a first of a rod lenses sub-chain 202 and a second rod lenses sub-chain 204. Sub-chain 202 includes similar rod lenses (not referenced) to sub-chain 204. However, the lenses of sub-chain 204 are inversely ordered and inversely oriented. That is, the distal lens of sub-chain 202 is the proximal lens of sub-chain 204 inversely oriented (i.e., the left surface is facing to the right and the right surface is facing to the left). Put another way, the structure of sub-chain 204 is a mirror image of the structure of sub-chain 202.

Sub-chains 202 and 204, together with a plurality of additional similar sub-chains constitute the relay system of a stereoscopic endoscope (e.g., relay system 104 of endoscope 100 of FIG. 1A). A series of images of the object plane and a series of pupil planes are repeatedly reimaged by the rod lenses chain (i.e., object imaging and pupil imaging). In the example set forth in FIG. 2, an $N^{th}$ intermediate image 206 of the object plane is positioned distally to sub-chain 202, an $N^{th}$ intermediate pupil plane image 208 is positioned between sub-chain 202 and sub-chain 204 and an $(N+1)^{th}$ intermediate object plane image 210 is positioned proximally to sub-chain 204. That is, light reflected from the object, travels from the direction of $N^{th}$ intermediate image 206 through sub-chain 202, $N^{th}$ intermediate pupil plane 208 and sub-chain 204 toward $(N+1)^{th}$ intermediate image 210. $(N+1)^{th}$ intermediate image 210 is reimaging of $N^{th}$ intermediate image 206 by rod-lenses chains 202 and 204.

As mentioned above, the dual-pupil aperture is periodically reimaged by the optical relay system. The channels associated with each pupil are fully separated, on any one of the pupil plane images. Thus, the channels can be separated (e.g., by employing a channel separator as mentioned in FIG. 1A) for detecting each channel by a separate image sensor.

As can be seen in FIG. 2, the exemplary light beams (depicted as dotted lines) occupy substantially fully the cross section of the rod lenses of sub-chains 202 and 204. In particular, the dual-pupil aperture image, when relayed along the relay system, occupies substantially fully the cross section of the relay system, in at least one location along the relay system.

Figure 3:
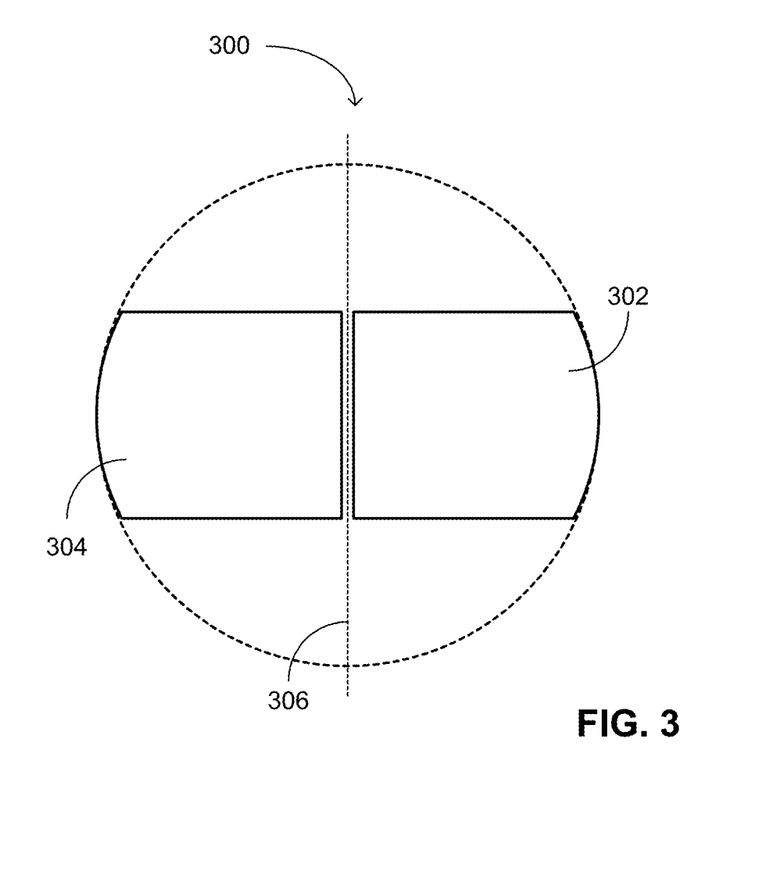
FIG. 3 is a schematic illustration of a dual-pupil, constructed and operative in accordance with a further embodiment of the disclosed technique.

Reference is now made to FIG. 3, which is a schematic illustration of a dual-pupil, generally referenced 300, constructed and operative in accordance with a further embodiment of the disclosed technique. Dual-pupil aperture 300 includes a first channel pupil 302 and a second channel pupil 304 (e.g., left and right perspective pupils). Each of first channel pupil 302 and second channel pupil 304 is in the shape of half of a circle, or a portion of half a circle. First channel pupil 302 and second channel pupil 304 are positioned adjacent to each other and complement each other for forming together a partial or full circle.

A line 306 marks the boundary between first channel pupil 302 and second channel pupil 304. The height of each pupil, as presented, is approximately equal to width of each pupil. In this manner, the resolution of each of first channel having pupil 302 and second channel having pupil 304 is similar in both the Y axis (i.e., the vertical axis) and the X axis (the horizontal axis). Each of first channel pupil 302 and second channel pupil 304 receives light beams of a different perspective of the object for producing a stereoscopic image.

The pixel size of the sensor (e.g., sensors 114 and 116 of FIG. 1A) should be appropriate to specific Nyquist criteria for avoiding aliasing of the image. The Nyquist frequency determining the pixel size is substantially about the spatial cutoff frequency of the optical system:

$$f_0 = \frac{1}{\lambda \times (f/\#)} \quad (1)$$

where '$f_0$' is the spatial cutoff frequency of the optical system, '$\lambda$' is the average wavelength of the light beams recorded (or absorbed) by the sensors 116, and 'f/#' is the $F_{number}$ of the optical system. It is noted that the beams reflected from the object have much larger spectrum than those recorded by the sensors. The size of the pixel, for avoiding aliasing, is proportional to the $F_{number}$ of the optical system. The $F_{number}$ of the optical system (e.g., endoscope 100) is inversely proportional to the size of each pupil of dual-pupil aperture 300. From all of the above, the maximal pixel size for avoiding aliasing is related to, and in particular decreases with, the size of the pupil.

The dual-pupil aperture is reimaged periodically along the optical relay system of the endoscope (e.g., relay system 104 of endoscope 100 of FIG. 1A). The dual-pupil aperture image substantially fully occupies the cross section of the optical relay system in at least one location of the optical relay system. In this manner, the pupil size is maximal for given dimensions of the optical relay system cross section, thereby allowing higher spatial cutoff frequency (i.e., better effective resolution) of the system than with conventional pupils, such as circular pupils. Additionally, the pupils of the dual-pupil aperture are reimaged at the distal end of endoscope (e.g., reimaged pupils 142A and 142B of FIG. 1B) such that the pupils are spatially separated from each other, thereby defining the IPD of the endoscope.

Figure 4A:
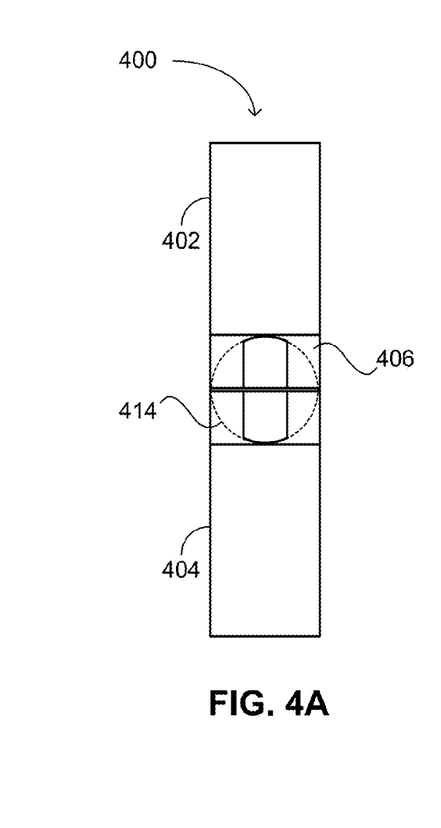
FIGS. 4A, 4B and 4C are schematic illustrations of periscope prisms, constructed and operative in accordance with yet another embodiment of the disclosed technique.
Figure 4B:
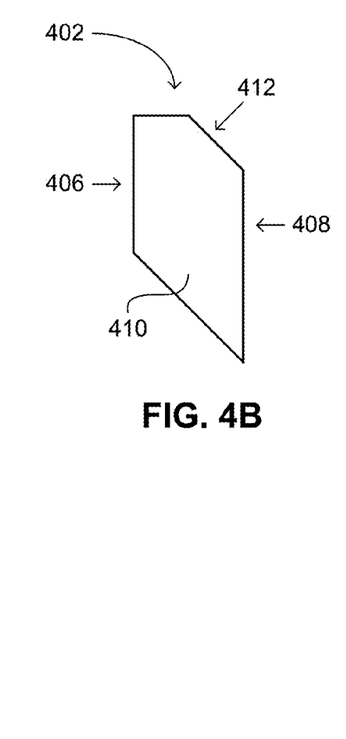
Figure 4C:
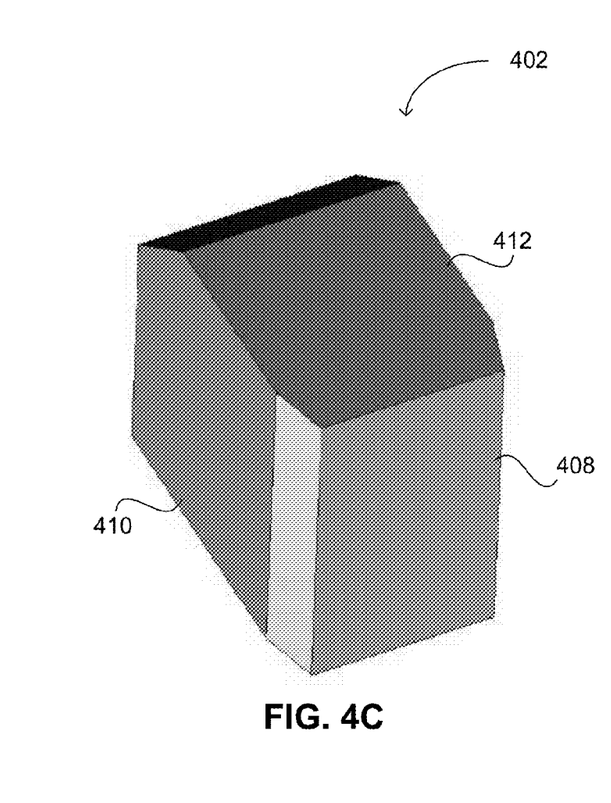

Reference is now made to FIGS. 4A, 4B and 4C, which are schematic illustrations of periscope prisms, generally referenced 400, constructed and operative in accordance with yet another embodiment of the disclosed technique. FIG. 4A depicts the periscope prisms from a front view perspective. FIG. 4B depicts one of the periscope prisms from a side view perspective. FIG. 4C depicts one of the periscope prisms from an isometric (top-back-side) view perspective.

With reference to FIG. 4A, periscope prisms 400 include a first periscope prism 402 and a second periscope prism 404. Prisms 402 and 404 are similar, and are placed oppositely adjacent one to the other. Periscope prism 402 includes an entrance surface 406 and exit surface 408 (FIG. 4B), similarly, periscope prism 404 also includes an entrance and exit surfaces (not referenced). The exit surfaces of prisms 402 and 404 are triangular and are positioned adjacent to each other, such that they complement each other and together form a square shape (not referenced).

An image of a dual-pupil (e.g., dual-pupil 106 of endoscope 100 of FIG. 1A) is depicted as a dotted circle 414 on the square formed by the entrance surfaces of the prisms. Thus, only the portions of the light transmitted through dual-pupil image 414 would impinge on the actual dual-pupil and would afterwards be detected by the sensors. As can be seen in FIG. 4A, the boundary between the pupils of dual-pupil image 414 corresponds to the chamfering of the entrance surfaces of distal periscope prisms 402 and 404. In this manner, the dimension in the first principle axis (e.g., vertical axis) of each pupil is the same as the dimension in the second principle axis (e.g., horizontal axis). Thereby, the resolution in each of the principle axes of each pupil is similar. Alternatively, other chamfering angles of the exit surfaces of the distal periscope prisms are possible (e.g., diagonal chamfering).

With reference to FIG. 4B, entrance surface 406, exit surface 408, side surface 410 (facing the viewer) and top surface 412 are indicated. With reference to FIG. 4C, exit surface 408, side surface 410 and top surface 412 are indicated. Front surface 406 is not shown from the top-back-side isometric perspective depicted in FIG. 4C.

Figure 05A:
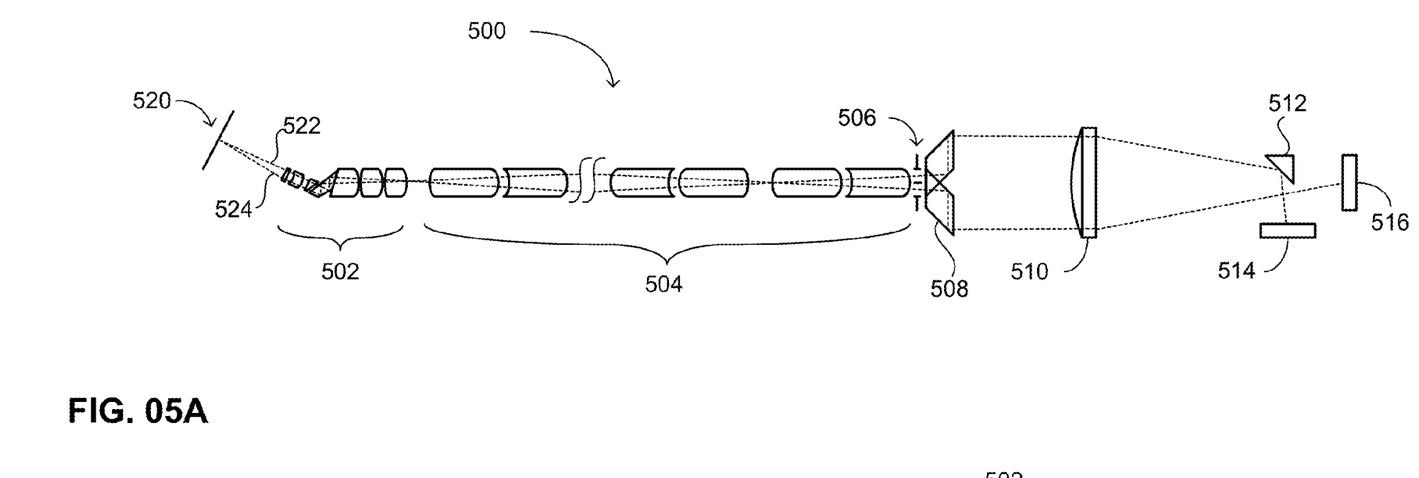
FIGS. 5A and 5B are schematic illustrations of a rotatable, oblique-viewing stereoendoscope, constructed and operative in accordance with yet a further embodiment of the disclosed technique.
Figure 05B:
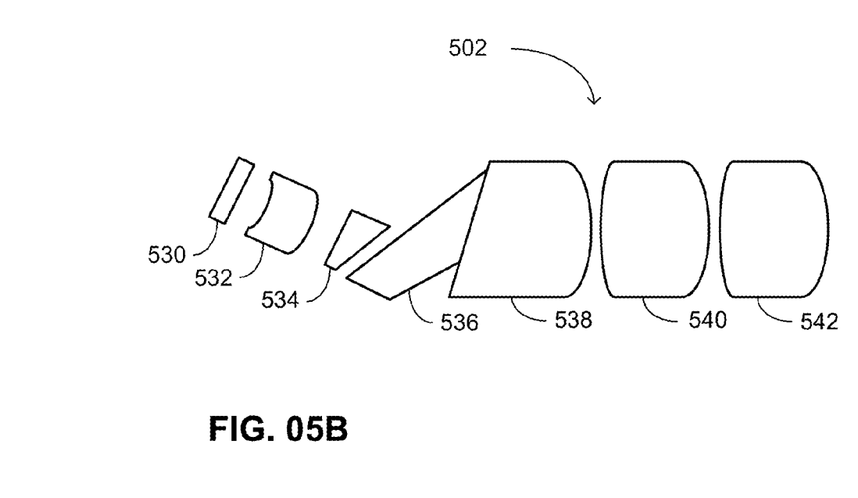

Reference is now made to FIGS. 5A and 5B, which are schematic illustrations of a rotatable, oblique-viewing stereoendoscope, generally referenced 500, constructed and operative in accordance with an embodiment of the disclosed technique. FIG. 5A depicts the optical components of the endoscope, and FIG. 5B depicts a front optical system and a folding prism of the endoscope in a magnified manner. Stereoscopic endoscope 500 includes a front optical system 502, a relay optical system 504, a dual-pupil aperture 506, a pair of proximal periscope prisms 508, a proximal objective lens assembly 510, a channel separator 512, two sensors 514 and 516.

Front optical system 502 is positioned distally to, and is optically coupled with, relay optical system 504. Dual-pupil aperture 506 is optically coupled between relay optical system 504 and proximal periscope prisms 508. Proximal objective lens assembly 510 is optically coupled between proximal periscope prisms 508 and channel separator 512. Channel separator 512 is further optically coupled with at least one of sensors 516.

An object plane 520 is positioned distally to front optical system 502 and at an angle with respect to the optical axis of relay system 504. Object plane 520 represents the surface of an object (or a scene) to be imaged. Object plane 520 is illuminated by a light source (not shown) either directly or through means, such as a fibers bundle or a light-guide.

Each of relay optical system 504, dual-pupil aperture 506, pair of proximal periscope prisms 508, proximal objective lens assembly 510, channel separator 512, two sensors 514 and 516 is substantially similar to each of relay optical system 104, dual-pupil aperture 106, pair of proximal periscope prisms 108, proximal objective lens assembly 110, channel separator 112, two sensors 114 and 116 of FIG. 1A, respectively. For the sake of brevity, the description of FIGS. 5A and 5B herein below would elaborate mainly on the components of stereoendoscope 500 that are different than those of stereoendoscope 100 of FIGS. 1A and 1B.

Front optical system 502 folds (i.e., bends at an oblique angle) the optical axis of stereoendoscope 500 by a folding prism 536 (FIG. 5B). Folding prism 536 is configured to fold the optical axis of endoscope 500 such that its FOV would be inclined at an oblique angle with respect to the optical axis of relay system 504. In the example set forth in FIGS. 5A and 5B, the folding prism is a double folding prism reflecting the light twice, and the folding prism folds the FOV of endoscope 500 by an angle of 30°. Alternatively, the folding angle of the prism can be any angle ranging between 0-90 degrees.

Additionally front optical system 502 (including folding prism 536) is rotatable and can rotate about the longitudinal axis (not shown) of relay system 504, thereby changing the DOV of endoscope 500. Front optical system 502 transmits light reflected from object plane 120 onto relay system 504. It is noted that in every direction that folding prism 536 (and front optical system 502) is directed to, folding prism 536 projects a plane toward relay system 504 and the projected plane is stereoscopically imaged by endoscope 500.

As dual-pupil aperture does not rotate, the stereoscopic image is always aligned and no other image direction alignment is required. Specifically, the projected plane (e.g., object plane 120) is always imaged such that the parallax between two optical channels of the endoscope (i.e., forming the stereoscopic image) is horizontal. In other words, for each rotation direction of front optical system 502, the folding prism would project a plane (e.g., object plane 120) onto relay system 504 and thereafter onto dual-pupil aperture 506. This projected plane would always (i.e., for every rotation angle) be imaged with a horizontal parallax allowing for stereopsis.

In accordance with another embodiment of the disclosed technique, relay system 504 is also rotatable and is rotated with front optical system 502, with respect to dual-pupil aperture 506. It is noted that relay system 504 is symmetric around its longitudinal axis, such that its stance (i.e., its current angle of rotation around the longitudinal axis) do not affect the relayed images. That is, relay system 504 can either be rotated with front optical system 502, or not, without any optical consequences.

Front optical system 502 reimages the pupils of endoscope 500 (i.e., dual-pupil aperture 506) at a point distal to front optical system 502. Specifically front optical system 502 reimage the pupils of endoscope 500 onto window 530 (FIG. 5B). Thereby, light reflected from object plane is received by the reimaged pupils and therefrom enters endoscope 500 and is eventually stereoscopically imaged. Front optical system 502 transmits the light reflected from object plane 118 in two separate channels 522 and 524 toward relay system 504 (each channel running between the reimaged respective pupil to a respective one of sensors 514 and 516). The components and configuration of front optical system 502 is detailed further herein below with reference to FIG. 5B.

Relay system 504 is both object imaging and pupil imaging. As mentioned herein above, relay system 504 may be static, such that front optical system 502 rotates with respect thereto. Alternatively, relay system 504 may be rotatable and be rotated with front optical system 502 with respect to dual-pupil aperture 506. Relay system 504 transmits the entering light beams through dual-pupil aperture 506 and onto proximal periscope prisms 508. Dual-pupil aperture 506 is constructed of an aperture stop and an opening (both not shown), and is divided into two pupils defining the two channels of endoscope 500.

Proximal periscope prisms 508 enlarge the distance between beams from each of the pupils of dual-pupil aperture 506 for adjusting the angular and spatial separation between those light beams for purpose of proper beam separation, such that each image would be directed to the respective one of sensors 514 and 516. Proximal objective lens assembly 510 focuses beams exiting proximal periscope prisms 510 onto sensors 514 and 516. Folding element 512 folds one the channels toward image sensor 514, while the other channel travels to sensor 516 (passing aside of folding element 512). Each of sensors 514 and 516 detects a respective image of object plane 120 received from a different perspective (the IPD between the reimaged pupils at the distal end of the front optical system). Thereby, stereoendoscope 500 acquires a stereoscopic image of object plane 120.

Each of proximal periscope prisms 508, proximal objective lens assembly 510, folding element 512 and sensors 514 and 516 are positioned at the proximal end of endoscope 500 and outside of the body of a patient. Therefore those elements are not subject to the physical constraints of minimally invasive surgery and can be of any size. Thereby, the size and resolution of sensors 514 and 516 can be increased to increase the Nyquist frequency of endoscope 500, thereby avoiding aliasing of the stereoscopic images.

With reference to FIG. 5B, front optical system 502 includes a distal window 530, a distal positive lens 532, a wedge 534, a folding prism 536, a spheroprism 538, a lens 540 and a lens 542. The optical components of front optical systems are arranged according to the order of their respective reference numerals from distal window 530 at the distal end to lens 542 at the proximal end of front system 502.

Front optical system 502 re-images dual-pupil 506 onto window 530 (i.e., onto the distal end of endoscope 500). Additionally, front optical system 502 re-images object plane 520, as seen from two spaced apart perspectives onto the focal plane of relay system 504. Thus, relay system 504 transmits the re-imaged object plane toward the sensors for detecting a stereoscopic image of object plane 520.

As mentioned above with reference to FIG. 1A, by re-imaging the pupils to the distal end of the stereoendoscope allows for detecting a large FOV. For enabling a wide FOV, stereoendoscope 500 does not include a negative lens (or a negative lens assembly) at the distal end thereof. Such a negative lens would have diverged the entering light, thereby limiting the entrance angle of the endoscope. Put another way, lens 532 is a positive power lens.

In accordance with another embodiment of the disclosed technique, a Diffractive Optical Element (DOE) can be added to the stereoendoscope (e.g., endoscope 100 of FIGS. 1A and 1B). The DOE is configured to compensate for accumulated spectral aberration, which is appearing owing to the relatively long optical path of the endoscope.

It will be appreciated by persons skilled in the art that the disclosed technique is not limited to what has been particularly shown and described hereinabove. Rather the scope of the disclosed technique is defined only by the claims, which follow.

The invention claimed is:

1. Rotatable, oblique-viewing stereoendoscope comprising:
    a dual-pupil aperture divided to a first pupil and a second pupil, said first pupil being configured to receive a first image of an object, said second pupil being configured to receive a second image of an object;
    a proximal objective assembly positioned proximally to said dual-pupil aperture, said proximal objective assembly being configured to focus said first image and said second image;
    a first image sensor configured to detect said first image focused by said proximal objective assembly, and a second image sensor configured to detect said second image focused by said proximal objective assembly;
    a relay system positioned distally to said dual-pupil aperture, said relay system being configured to transmit said first image and said second image toward said dual-pupil aperture;
    a front optical system positioned distally to said relay system, said front optical system being further configured to produce said first image from said reflected light received through said image of said first pupil and to produce said second image from said reflected light received through said image of said second pupil; and
    said front optical system comprising a folding prism, said folding prism being configured to receive reflected light reflected from said object and to direct said reflected light at an oblique angle toward said relay system, said folding prism enabling a horizontal parallax between an optical channel of said first pupil and an optical channel of said second pupil, said folding prism being rotatable with respect to said dual-pupil aperture such that a direction of view of said stereoendoscope can be rotated about a longitudinal axis of said relay system, wherein said front optical system being configured to reimage said dual-pupil aperture at a distal end thereof, thereby producing an image of said first pupil and an image of said second pupil at a distal pupil plane,
    and wherein said folding prism is a double folding prism.

2. The stereoendoscope of claim 1, wherein said proximal objective assembly, said first image sensor, and said second image sensor are positioned externally to a body of a subject.

3. The stereoendoscope of claim 1, wherein said front optical system comprises proximal periscope prisms and a common lens assembly, and wherein said common lens assembly is configured to reimage said first pupil and said second pupil distally to said proximal periscope prisms, such that a reimaged first pupil located distally to said proximal periscope prisms and a reimaged second pupil located distally to said proximal periscope prisms, are spatially separated.

4. The stereoendoscope of claim 3, wherein said front optical system further comprises a first channel lens assembly and a second channel lens assembly, and wherein said proximal periscope prisms direct said first image from said first channel lens assembly, and said second image from said second channel lens assembly, toward said relay system.

5. The stereoendoscope of claim 4, wherein each of said first channel lens assembly is configured to reimage said first pupil distally to said first channel lens assembly, and wherein said second channel lens assembly is configured to reimage said second pupil distally to said second channel lens assembly.

6. The stereoendoscope of claim 1, wherein at said distal pupil plane said image of said first pupil and said image of said second pupil are spatially separated thereby defining an Inter Pupillary Distance of said stereoendoscope.

7. The stereoendoscope of claim 1, wherein said front optical system includes said folding prism, and is rotatable with said folding prism.

8. The stereoendoscope of claim 7, wherein said front optical system further includes a spheroprism proximally adjacent to said folding prism.

* * * * *